US007232450B2

(12) United States Patent
Gorans et al.

(10) Patent No.: US 7,232,450 B2
(45) Date of Patent: Jun. 19, 2007

(54) APPARATUS AND METHOD FOR UPPER AND LOWER BEAK TREATMENT

(75) Inventors: Marc S. Gorans, Willmar, MN (US); Matthew H. Erickson, Raymond, MN (US)

(73) Assignee: Nova-Tech Engineering, Inc., Willmar, MN (US)

( * ) Notice: Subject to any disclaimer, the term of this patent is extended or adjusted under 35 U.S.C. 154(b) by 606 days.

(21) Appl. No.: 10/346,981

(22) Filed: Jan. 17, 2003

(65) Prior Publication Data

US 2004/0143278 A1 Jul. 22, 2004

(51) Int. Cl.
*A61B 18/04* (2006.01)
*A61D 1/04* (2006.01)

(52) U.S. Cl. ...................................................... 606/164

(58) Field of Classification Search ................ 606/164, 606/163, 15, 16, 9; 604/115, 144; 607/88, 607/94; 452/166

See application file for complete search history.

(56) References Cited

U.S. PATENT DOCUMENTS 2,448,421 A 8/1948 Davis
2,484,088 A 10/1949 Hayes
2,501,283 A 3/1950 McKnight
2,505,559 A 4/1950 Lyon
2,713,325 A 7/1955 Bowers
2,731,016 A 1/1956 Miller
2,742,904 A 4/1956 Lyon
2,792,004 A 5/1957 Sandy
2,952,031 A 9/1960 Breitkreutz
3,136,315 A 6/1964 Lyon
3,274,974 A 9/1966 Reynolds
3,295,524 A 1/1967 Parker
3,302,645 A 2/1967 Lockmiller
3,502,079 A 3/1970 Simmons
3,570,487 A 3/1971 Reynolds
3,593,714 A 7/1971 Lyon
3,623,186 A 11/1971 Panek
3,964,481 A 6/1976 Gourlandt et al.
3,994,292 A 11/1976 Goodwin
4,019,513 A 4/1977 Kaniecki
4,026,289 A 5/1977 Hendrix
4,040,425 A 8/1977 Goodling et al.
4,177,810 A 12/1979 Gourlandt
4,191,130 A 3/1980 Musgrave
4,343,310 A 8/1982 DuBose et al.
4,375,814 A 3/1983 Gourlandt (Continued)

FOREIGN PATENT DOCUMENTS

NL 8 802 812 6/1990

*Primary Examiner*—Michael J. Hayes
*Assistant Examiner*—M. Thomas Andersen
(74) *Attorney, Agent, or Firm*—Mueting, Raasch & Gebhardt, P.A.

(57) ABSTRACT

Apparatus and methods for treating the upper and lower beaks of poultry by non-contact heating of the upper and lower beaks of the bird are disclosed. The upper and lower beak treatment may include delivery of energy to the upper and lower beak in amounts sufficient to retard the growth and/or result in erosion of portions of both the upper beak and the lower beak. The energy incident on the lower beak may be reflected from a lower beak energy director (e.g., a reflector) or it may be provided a separate energy source.

16 Claims, 5 Drawing Sheets

U.S. PATENT DOCUMENTS

| | | | | | |
|---|---|---|---|---|---|
| RE31,202 | E | | 4/1983 | Goodling et al. | |
| 4,446,819 | A | | 5/1984 | Gourlandt | |
| 4,681,565 | A | | 7/1987 | Gourlandt | |
| 4,951,610 | A | * | 8/1990 | Gourlandt | 606/163 |
| 5,195,925 | A | | 3/1993 | Gorans | |
| 5,441,531 | A | * | 8/1995 | Zarate et al. | 607/90 |
| 5,651,731 | A | * | 7/1997 | Gorans et al. | 606/164 |
| 5,782,895 | A | * | 7/1998 | Zarate et al. | 607/88 |
| 6,413,268 | B1 | * | 7/2002 | Hartman | 607/94 |
| RE38,670 | E | * | 12/2004 | Asah et al. | 606/9 |
| 6,942,657 | B2 | * | 9/2005 | Sinofsky et al. | 606/15 |
| 6,942,658 | B1 | * | 9/2005 | Rizoiu et al. | 606/16 |

* cited by examiner

FIG. 5
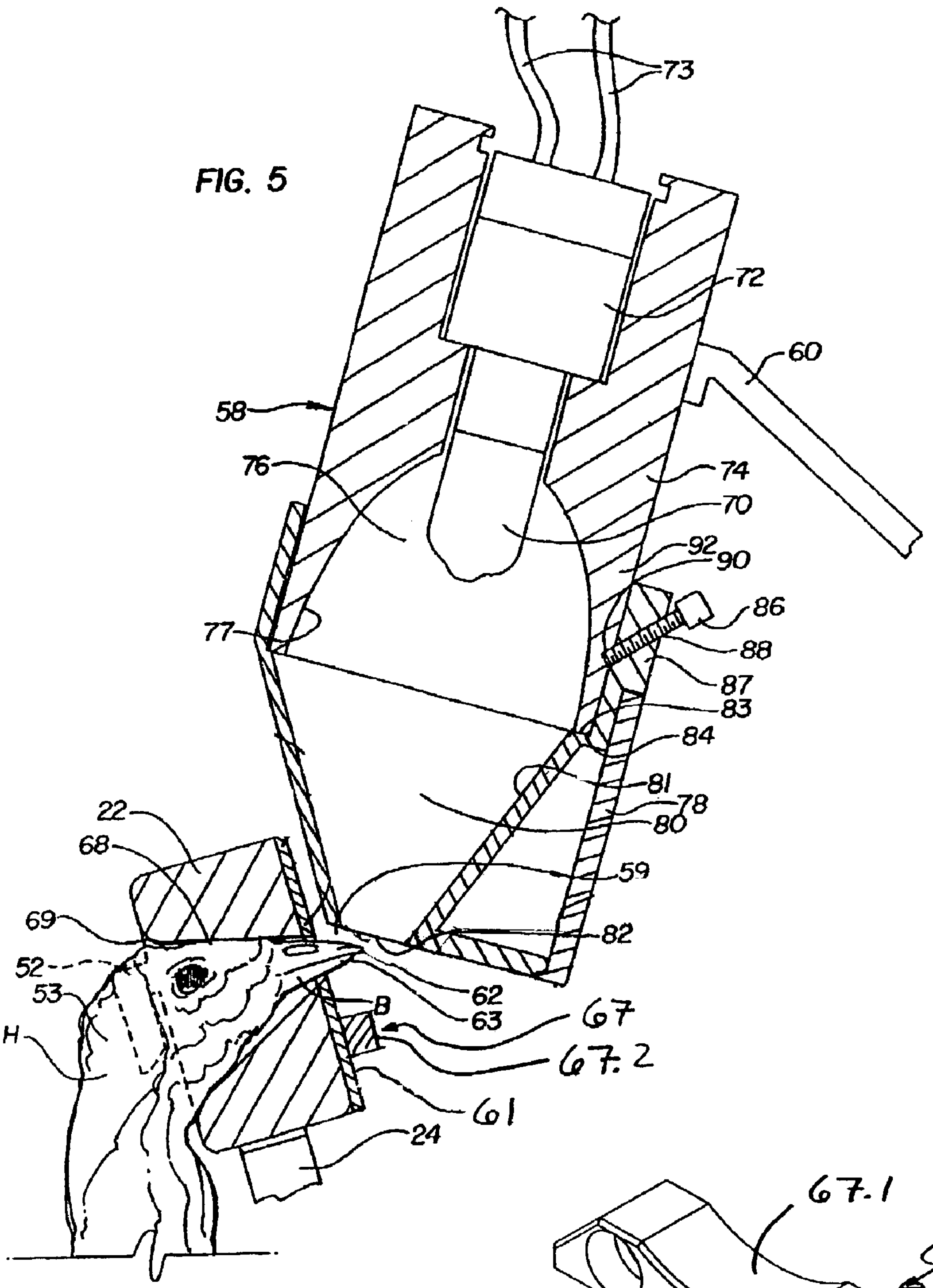
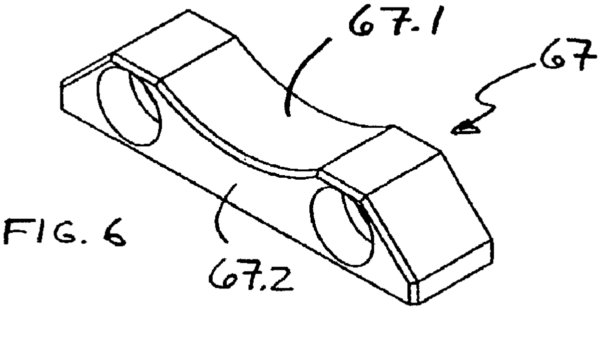
FIG. 6

APPARATUS AND METHOD FOR UPPER AND LOWER BEAK TREATMENT

BACKGROUND

The beak of a bird is a weapon and a tool for eating. In commercial production, poultry are raised in close proximity to each other. In this environment, young birds may use their beaks for pecking other birds, potentially causing disfigurement, illness, or death. The sharp tip of the beak is the most dangerous part of the beak. In addition, adult poultry may use their beaks as weapons to damage other adult and juvenile poultry. This use of the beak as a weapon causes economic losses for the poultry producer. Accordingly, a portion of the beak is typically removed from poultry to minimize its effectiveness as a weapon.

Previously, debeaking methods were based on the principle of killing all tissue just ahead of the nostril by severing the blood supply and generally destroying the tissue of the beak. This was done through cutting the beak with a blade or by bringing the beak in contact with a hot object to burn through the beak. Although bleeding may be minimized by cauterization, the wound resulting from these processes produced a substantial amount of pain and shock in the bird.

In using these prior art processes, precision positioning of the beak and ineffectiveness of the method used resulted in several disadvantages. For example, the beak could heal and regenerate if the blood supply to the beak was not completely cut. Furthermore, when the veins are cut close to the nostril, they are large and difficult to seal resulting in problems avoiding infection or bleeding. The prior art method also could induce severe shock and pain to the bird.

U.S. Pat. No. 5,651,731 (Gorans et al.) addresses many of these issues. For example, the apparatus and methods described therein provide a more humane method for treating the beaks of poultry because the method is bloodless, induces little or no shock, and minimizes damage to the bird. It did not, however, address the issue of retardation in growth of the lower beak of a bird. In fact, the method and apparatus were specifically designed to avoid treating the lower beak of the bird. Allowing the lower beak to grow without interference may, however, allow some species of birds (e.g., chickens) to scatter significant amounts of food using that lower beak. The scattered food is typically wasted and does not contribute to the nutrition of the bird.

Another issue that may be raised by treating only the upper beak of a bird is that mating behavior may be adversely affected. In some species of birds, e.g., chickens, the male bird typically grasps the female in his beak during mating. If the male's lower beak extends past the upper beak, the male's ability to grasp the female may be inhibited, thereby adversely affecting mating behavior and/or success.

SUMMARY OF THE INVENTION

The present invention provides apparatus and methods for treating the upper and lower beaks of poultry by non-contact heating of the upper and lower beaks of the bird. Although it may be desirable that some species of birds retain their lower beaks without any change after beak treatment, it may be more desirable to retard the growth of the lower beak in other species (e.g., chickens).

It may be preferred tat the upper and lower beak treatment include delivery of energy to the upper and lower beak in amounts sufficient to retard the growth and/or result in erosion of portions of both the upper beak and the lower beak. The energy incident on the lower beak may be reflected from a lower beak energy director (e.g, a reflector) or it may be provided by a separate energy source. It maybe preferred tat the amount of energy delivered to the lower beak be less than the amount of energy delivered to the upper beak. That selective delivery may be accomplished by using only reflected energy to treat the lower beak, while using direct energy from the source to treat the upper beak.

As used in connection with the present invention, a "non-contact energy source" means an energy source that is capable of heating the beak of a live bird without physical contact of a solid object such as a heated wire, heated blade, etc. Examples of suitable non-contact energy sources include, but are not limited to, lasers, bulbs emitting infrared radiation, heated fluids, etc.

Advantages of the present invention may include the ability to treat both the upper and lower beaks of a bird in a single operation, preferably (but not necessarily) simultaneously. Retarding the growth in both the upper and lower beaks such that they have a similar length can reduce food waste and/or improve mating success for some birds.

Other potential advantages of the apparatus and methods of the present invention are that the bird's eyes and nostrils may be shielded from scattered energy applied during the treatment; the upper and lower beaks may be precisely positioned during treatment; tolerance in beak size variation between birds; and uniform depth of penetration of the energy typically results in damage to the interior of the beak being most severe at the tip and reducing as the beak gets thicker towards the bird's nostril. Still other potential advantages may include retention of the upper and lower beaks for one to two weeks to help the bird learn to eat and drink before the exposed beak structure is lost; as well as control over the depth of penetration of the radiated heat into the beak by adjusting the power rate and exposure time used.

In one aspect, the present invention provides an apparatus for treating the upper and lower beaks of a bird, the apparatus including a bird head positioning device having first and second major sides and a beak receiving aperture formed through the first and second major sides. The bird head positioning device is adapted to position the head of a bird proximate the first major side, wherein the upper and lower beaks of the bird head protrude through the beak receiving aperture and are exposed proximate the second major side of the bird head positioning device. The apparatus also includes a non-contact energy source emitting energy, and a primary energy director directing energy from the non-contact energy source at the second major surface of the beak locator. Energy emitted from the non-contact energy source is directly incident on the upper beak exposed proximate the second major side of the bird head positioning device. The apparatus further includes a secondary energy director redirecting energy from the primary energy director towards the lower beak exposed proximate the second major side of the bird head positioning device.

In another aspect, the present invention provides an apparatus for treating the upper and lower beaks of a bird, the apparatus including a bird head positioning device having first and second major sides and a beak receiving aperture formed through the first and second major sides. The bird head positioning device is adapted to position the head of a bird proximate the first major side, wherein the upper and lower beaks of the bird head protrude through the beak receiving aperture and are exposed proximate the second major side of the bird head positioning device. The apparatus also includes a non-contact energy source emitting energy and a primary energy director directing energy from the non-contact energy source at the second major surface of the beak locator. Energy emitted from the non-contact energy source is directly incident on the lower beak exposed proximate the second major side of the bird head positioning device. The apparatus further includes a secondary energy director redirecting energy from the lower beak energy director towards the upper beak exposed proximate the second major side of the bird head positioning device.

In another aspect, the present invention provides an apparatus for treating the upper and lower beaks of a bird, the apparatus including a bird head positioning device having first and second major sides and a beak receiving aperture formed through the first and second major sides. The bird head positioning device is adapted to position the head of a bird proximate the first major side, wherein the upper and lower beaks of the bird head protrude through the beak receiving aperture and are exposed proximate the second major side of the bird head positioning device. The apparatus also includes a non-contact energy source emitting energy and an upper beak energy director directing energy from the non-contact energy source at the second major surface of the beak locator. Energy directed by the upper beak energy director is directly incident on the upper beak exposed proximate the second major side of the bird head positioning device. The apparatus further includes a lower beak energy director directing energy from the non-contact energy source at the second major surface of the beak locator, wherein energy directed by the lower beak energy director is directly incident on the lower beak exposed proximate the second major side of the bird head positioning device.

In another aspect, the present invention provides a method for treating the upper and lower beaks of a bird by positioning a bird head in a bird head positioning device, wherein the bird head positioning device comprises first and second major sides and a beak receiving aperture formed through the first and second major sides. The upper and lower beaks of the bird head protrude through the beak receiving aperture and are exposed proximate the second major side of the bird head positioning device. The method also includes emitting energy from a non-contact energy source and directing the energy emitted from the non-contact energy source at the second major surface of the bird head positioning device using a primary energy director. The energy directed by the primary energy director is directly incident on the upper beak exposed proximate the second major side of the bird head positioning device. The method further includes redirecting energy from the primary energy director using a secondary energy director towards the lower beak exposed proximate the second major side of the bird head positioning device.

In another aspect, the present invention provides a method for treating the upper and lower beaks of a bird by positioning a bird head in a bird head positioning device, wherein the bird head positioning device comprises first and second major sides and a beak receiving aperture formed through the first and second major sides. The upper and lower beaks of the bird head protrude through the beak receiving aperture and are exposed proximate the second major side of the bird head positioning device. The method also includes emitting energy from a non-contact energy source and directing the energy emitted from the non-contact energy source at the second major surface of the bird head positioning device using a primary energy director, wherein the energy directed by the primary energy director is directly incident on the lower beak exposed proximate the second major side of the bird head positioning device. The method further includes redirecting energy from the primary energy director using a secondary energy director towards the upper beak exposed proximate the second major side of the bird head positioning device.

In another aspect, the present invention provides a method for treating the upper and lower beaks of a bird by positioning a bird head in a bird head positioning device, wherein the bird head positioning device includes first and second major sides and a beak receiving aperture formed through the first and second major sides. The upper and lower beaks of the bird head protrude through the beak receiving aperture and are exposed proximate the second major side of the bird head positioning device. The method also includes directing energy at the second major surface of the bird head positioning device using an upper beak energy director. The energy directed by the upper beak energy director is directly incident on the upper beak exposed proximate the second major side of the bird head positioning device and the energy is absorbed by the upper beak in the absence of physical contact. The method further includes directing energy at the second major surface of the bird head positioning device using a lower beak energy director. The energy directed by the lower beak energy director is directly incident on the lower beak exposed proximate the second major side of the bird head positioning device and is absorbed by the lower beak in the absence of physical contact.

These and other features and advantages of the invention may be described in more detail below with respect to illustrative embodiments of the invention.

BRIEF DESCRIPTION OF THE DRAWING

FIG. 5 is a cross-sectional view taken along line 5—5 of FIG. 1.

FIG. 6 is a perspective view of one secondary energy director that may be used to direct energy in accordance with the present invention.

DETAILED DESCRIPTION OF ILLUSTRATIVE EMBODIMENTS OF THE INVENTION

In the following detailed description of illustrative embodiments, reference is made to the accompanying drawings that form a part hereof, and in which are shown, by way of illustration, specific embodiments in which the invention may be practiced. It is to be understood that other embodiments may be utilized and structural changes may be made without departing from the scope of the present invention. Furthermore, like reference numbers denote like features in the different figures.

Figure 1:
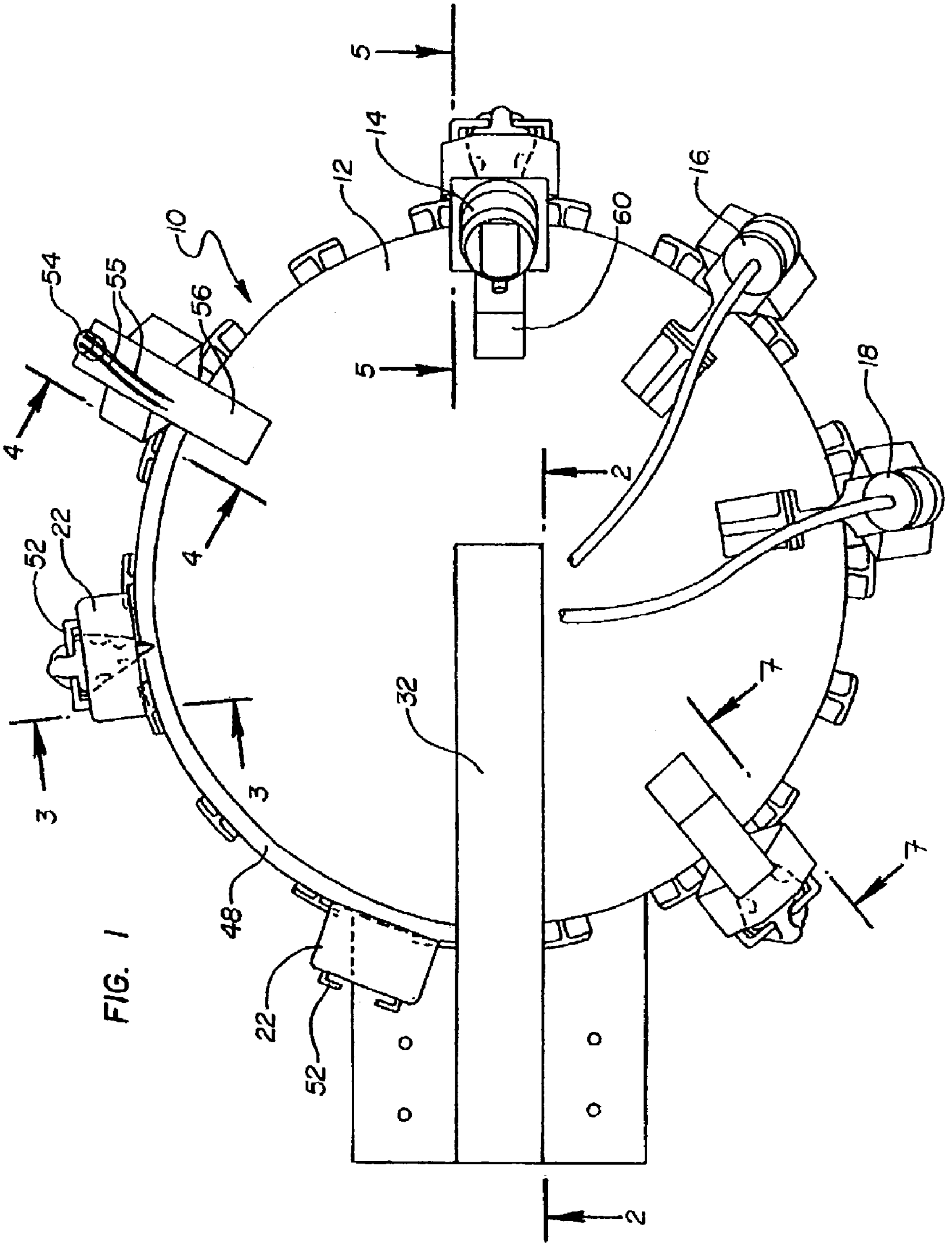
FIG. 1 is a plan view of a bird processing apparatus including a beak treatment station.

One apparatus for processing live poultry indicated in general by the numeral 10 is shown in FIG. 1. A mounting plate 12 supports beak treatment station 14, liquid injection station 16 and pellet injection station 18. Poultry P are secured in the bird head positioning device 22 and are preferably conveyed to the beak treatment station 14 before being unloaded from the head positioning device 22.

Figure 2:
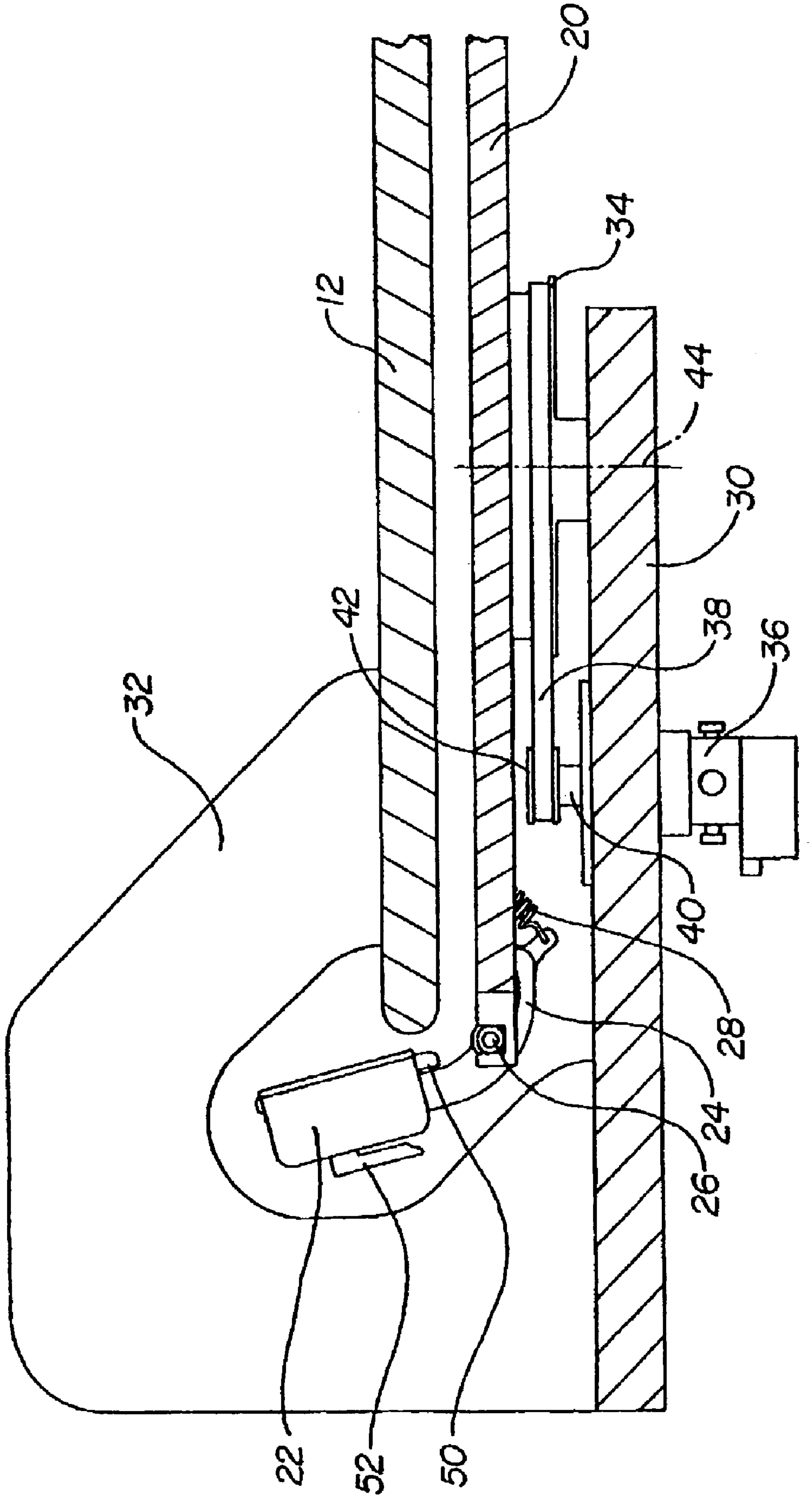
FIG. 2 is a cross-sectional view taken along line 2—2 of FIG. 1.

FIG. 2 is a cross-sectional view of one mounting arrangement between mounting plate 12 and platform 20. The bird head positioning device 22 may be attached to platform 20 by rocker arm 24 which is pivotally connected to platform 20 at head pin 26. In the depicted embodiment, spring 28 connects to rocker arm 24 to urge rocker arm 24 into a predetermined position about head pin 26. Spring 28 is connected to rocker arm 24 and platform 20 and may preferably flex to allow rocker arm 24 to pivot about head pin 26. Platform 20 is preferably rotatably mounted on base plate 30.

Mounting plate 12 is preferably attached to mounting arch 32. Processing stations 14, 16, and 18 are preferably mounted on plate 12. In the depicted embodiment, platform 20 is connected to drive pulley 34. Drive pulley 34 is connected to drive motor 36 by drive belt 38. Drive motor 36 is mounted on mounting plate 12 to allow drive motor 36 to rotate drive shaft 40 turning motor pulley 42 which is connected to drive pulley 34 with drive belt 38. As should be understood, drive motor 36 will rotate motor pulley 42 to cause drive belt 38 to transfer the rotary motion to drive pulley 34 causing platform 20 to rotate. Platform 20 and drive pulley 34 rotate about the same axis 44. Mounting arch 32 maintains a spaced relation between mounting plate and platform 20.

Figure 3:
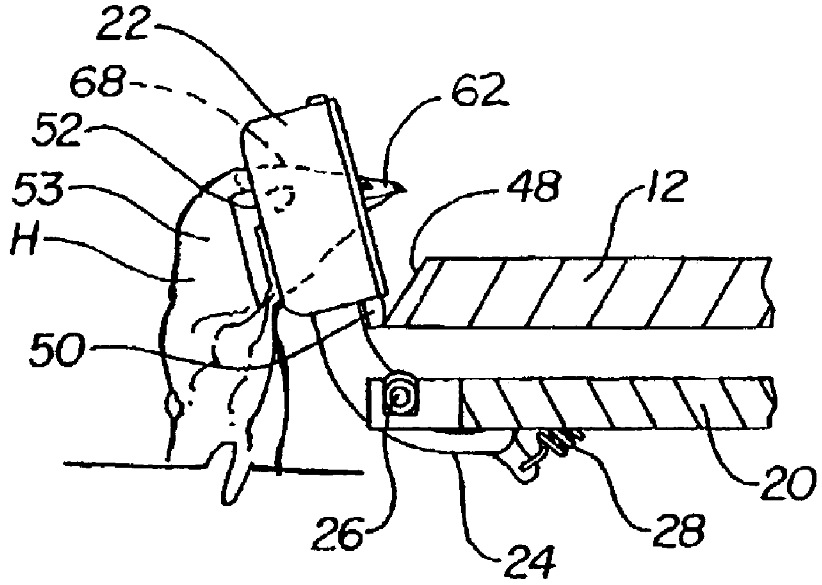
FIG. 3 is a cross-sectional view taken along line 3—3 of FIG. 1.

As seen in the embodiment of FIG. 1, bird head positioning device 22 travels clockwise from mounting arch 32 to interface with loading trigger ramp 48. FIG. 3 illustrates trigger ramp 48 which acts as a cam surface bearing against cam follower 50 to pivot skin bunchers 52 such that they engage the skin on bird's head. As poultry head H is placed into the bird head positioning device 22, cam follower 50 is urged into the engaged position, causing skin bunchers 52 to engage and retain poultry head H. Skin bunchers 52 are pivoted on head positioning device 22 to bunch the poultry skin at the back of bird's head. Bunched skin 53 may be used for other processing operations such as liquid injection or pellet injection.

Figure 4:
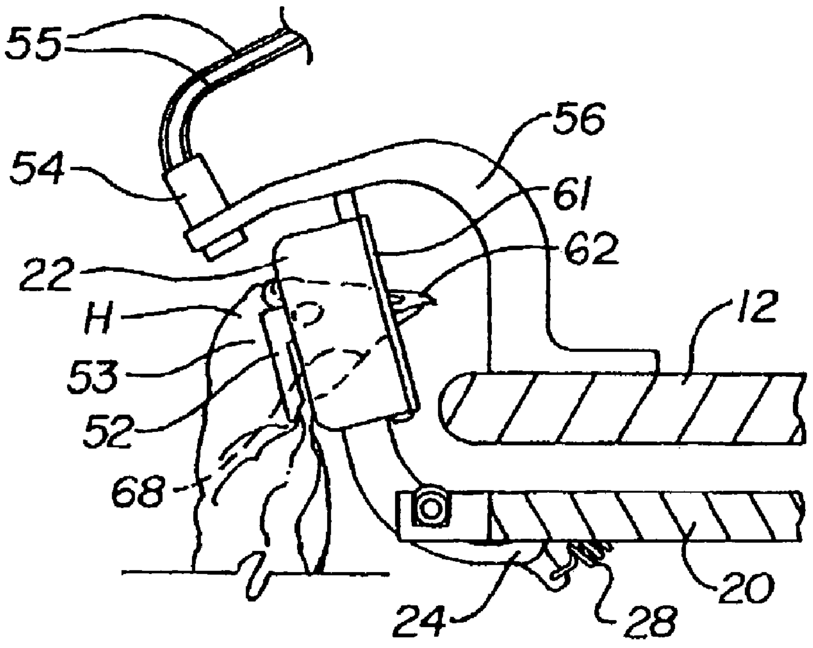
FIG. 4 is a cross-sectional view taken along line 4—4 of FIG. 1.

As bird head positioning device 22 is moved on platform 20 with respect to mounting plate 12, poultry head H is detected by bird sensing module 54. As illustrated in FIG. 4, bird sensing module 54 may be a capacitive moisture sensor module of the type manufactured by Omron, Turk, Banner and others. The detection of bird's head H by bird sensing module 54 causes an electrical signal that can be monitored by a control system through wires 55. Bird sensing module 54 is attached to mounting plate 12 by bird sensor support 56.

As illustrated in FIG. 5, the bird head positioning device 22 includes a beak receiving aperture 68 formed therein, the beak receiving aperture 68 extending from the first major side 69 of the bird head positioning device 22 through to the second major side 61 of the bird head positioning device 22. The beak receiving aperture 68 may preferably be sized and shaped to receive a portion of the bird's head H as shown to facilitate retention of the bird's head and accurate positioning of both the upper beak 62 and the lower beak 63 within the beak receiving aperture 68.

When in position as shown in FIG. 5, selected portions of the bird's upper beak 62 and lower beak 63 extend through the beak receiving aperture 68 and are exposed proximate the second major side 61 of the bird head positioning device 22. Those portions of the upper beak 62 and the lower beak 63 thus exposed are available for treatment as described herein.

FIG. 5 also depicts one embodiment of a non-contact energy source that may be used to emit the energy required for treatment of the beaks. The depicted non-contact energy source 58 (in the depicted embodiment) includes a housing 74 that is operably attached to the mounting plate 12 by bracket 60.

The non-contact energy source 58 of FIG. 5 includes a bulb 70 emitting light that can be directed onto the upper beak 62 and the lower beak 63 to effect beak treatment. The bulb 70 in the depicted embodiment is mounted in a lamp socket 72 that is electrically connected to a power supply (not shown) by electrical conductors 73.

The non-contact energy source 58 with bulb 70 is one embodiment of a non-contact energy source 58 that provides electromagnetic energy useful for treating the upper and lower beaks of birds in accordance with the present invention. One example of a suitable bulb 70 that may be used in connection with the present invention is a 350 watt Tungsten bulb (emitting electromagnetic energy in, e.g., the infrared spectrum from 700 nanometers to 1 millimeter), although a variety of energy emitting bulbs may be used. When selecting bulbs, it may be considered that bulbs with compact filament areas typically create less ambient heat and may be easier to focus.

As used herein, "electromagnetic energy" includes energy with wavelengths/frequencies suitable for delivering sufficient energy by radiation to the beak of a bird to effect thermal beak treatment as discussed herein. As such, it may be preferred that the electromagnetic energy be within the visible spectrum, the infrared spectrum, or a combination of the visible and infrared spectrums (although electromagnetic energy outside of those spectrums may be used if sufficient energy can be delivered to the beak via radiation to accomplish thermal beak treatment).

As accomplished in connection with the present invention, non-contact thermal beak treatment involves the delivery of energy by radiation or convection to a beak to penetrate the beak B. In the case of radiated electromagnetic energy, wavelength(s) may be selected that penetrate through the outer layers of the beak to the inner layers, killing a portion of the beak tissue thus exposed to the radiated electromagnetic energy and destroying the ability of the soft tissues of the inner beak to develop into hard tissue.

Bulb 70 is preferably positioned in elliptical reflector cavity 76 with a polished elliptical surface 77 that preferably reflects and focuses the electromagnetic energy emitted by bulb 70. The reflector cavity 76 is arranged to reflect electromagnetic energy emitted from the bulb into a primary energy director 78 that, in the depicted embodiment, takes the form of a tapered passage 80. The tapered passage 80 has a polished surfaced 81 extending to electromagnetic radiation aperture 82. Electromagnetic energy emitted by the bulb 70 exits from the primary energy director 78 through the aperture 82 which is preferably spaced from the upper beak 62 of the bird by a gap 59.

The primary energy director 78 may include a translucent window (not shown) transmissive to energy emitted by the bulb. Such a window may be mounted in aperture 82 to seal the cavity defined by tapered passage 80 and elliptical reflector cavity 76, thereby preventing smoke or other contaminants from entering the tapered passage 80 and elliptical reflector cavity 76.

In the depicted embodiment, the primary energy director 78 includes a mounting face 83 that cooperates with a mounting face 84 on the elliptical reflector body 74 to maintain proper spacing between the various components. A thumb screw 86 is threadably mounted in mounting hole 88 and extends through wall 87 of primary energy director 78. The thumb screw 86 extends into thumb screw seat 90 along peripheral wall 92 of elliptical reflector body 74 to secure the body 74 relative to the primary energy director 78.

As depicted in FIG. 5, the primary energy director 78 may be positioned such that energy emitted from the non-contact energy source 58 is directly incident on the portion of the upper beak 62 protruding from the beak receiving aperture 68, with the lower beak 63 being located within the shadow of the direct radiation exiting from the primary energy director 78.

Also depicted in FIG. 5 is a secondary energy director 67 that redirects energy from the primary energy director 78 towards the portion of the lower beak 63 protruding from the beak receiving aperture 68. The secondary energy director 67 essentially collects the energy that would otherwise pass by the upper beak 62 and redirects it towards the lower beak 63. Because the lower beak 63 receives only reflected energy, the lower beak 63 may receive less energy than the upper beak 62 (which receives direct energy). It may be preferred that the lower beak 63 receive less energy during beak treatment to prevent unwanted damage to the tongue of the bird.

The depicted secondary energy director 67 is mounted on the second major surface 61 of the bird head positioning device 22, although it may be mounted in a variety of other locations. Regardless of the mounting location, the secondary energy director 67 is preferably positioned and shaped to redirect energy emitted by the non-contact energy source 58 towards the lower beak 63 protruding from the beak receiving aperture 68.

FIG. 6 is a perspective view of one embodiment of the secondary energy director 67 seen in FIG. 5. The director 67 may include a curved reflective surface 67.1 designed to focus, as well as reflect, electromagnetic energy incident thereon. Focusing of the electromagnetic energy incident on the surface 67.1 may assist in the beak treatment process. Surface 67.2 is denoted in both FIGS. 5 & 6 to assist the viewer in determining the orientation of the reflective surface 67.1.

It will be understood that the exact shape of the secondary energy directors used in connection with the present invention may differ from that depicted in FIGS. 5 & 6. For example, the reflective surface may be planar if so desired. A planar reflective surface may be used if, e.g., the energy to be reflected is collimated. Other alternative focusing reflective surfaces may include, e.g., cup-shaped surfaces, surfaces including a number of planar facets, compound surfaces including both planar and curved facets, etc.

Furthermore, it will be understood that the arrangement of the non-contact energy source 58, the primary energy director 78, and secondary energy director 67 could be reversed relative to the upper and lower beaks 62 and 63 of the bird. In other words, the primary energy director 78 could be positioned such that electromagnetic energy exiting the primary energy director 78 is directly incident on the lower beak 63, while the secondary energy director 67 is positioned to direct electromagnetic energy on the upper beak 62.

In addition to being used to position the bird's head H and beak B as described herein, the bird head positioning device 22 may also preferably function to shield the portions of the beak B that do not protrude from the beak receiving aperture 68 from the radiated energy emitted by the non-contact energy source 58. The bird head positioning device 22 may also function to shield the bird's head H from the energy emitted by the non-contact energy source 58.

Figure 7:
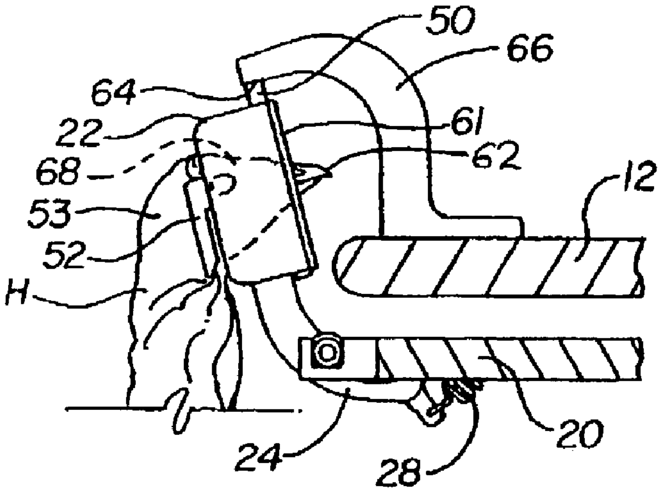
FIG. 7 is a cross-sectional view taken along line 7—7 of FIG. 1.

Upon completion of the beak treatment process, bird head positioning device 22 may be rotated into the position shown in FIG. 7 where unload cam surface 64 bears against cam follower 50 to cause skin bunchers 52 to pivot into the disengage position. Unload cam surface 64 is mounted on mounting plate 12 by unload support 66. Bird head positioning device 22 is then rotated on platform 20 to receive a new bird at the load station shown in FIG. 3.

Figure 8:
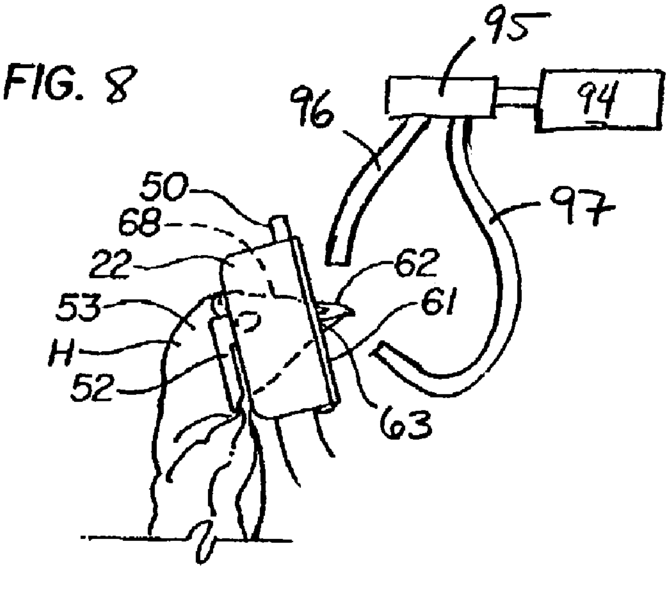
FIG. 8 is an alternative embodiment depicting a laser directing laser energy onto the upper and lower beaks of a bird

FIG. 8 depicts an alternative embodiment of the invention in which the electromagnetic energy used for beak treatment is provided by a laser 94. In this embodiment, the laser includes a beam splitter 95 separating the laser energy into two beams that are directed at the upper beak 62 and the lower beak 63 through energy directors 96 and 97 in the form of, e.g., fiber optic cables (depicted), mirrors, etc. Although a common energy source in the form of a single laser 94 is depicted in FIG. 8 with its output split to treat the upper and lower beaks 62 and 63, it will be understood that, alternatively, two different lasers may be used, with the energy from one laser being applied to the upper beak and energy from the second laser being applied to the lower beak.

Figure 9:
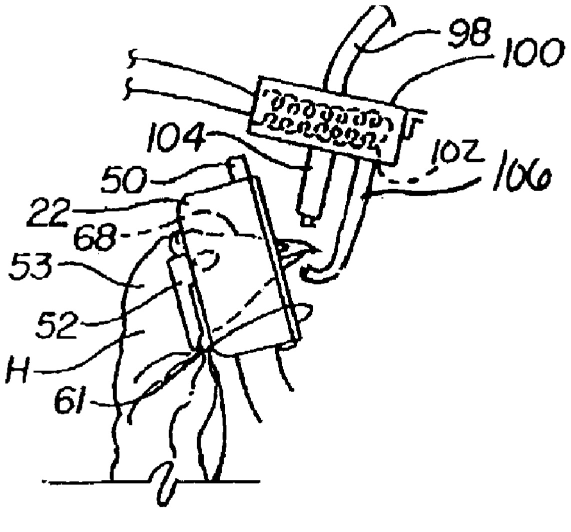
FIG. 9 is an alternative embodiment depicting a heated fluid delivery system for directing energy onto the upper and lower beaks of a bird.

In another alternative embodiment of the invention, FIG. 9 depicts the use of a heated fluid to accomplish the beak treatment process, wherein delivery of the non-contact energy is accomplished by convection. The heated fluid may typically be a heated gas, e.g., air, nitrogen, steam, etc. In the depicted embodiment, a supply tube 98 is connected to a source of pressurized gas. Supply tube 98 is also connected to a non-contact energy source 100 that, in the depicted embodiment, includes a heating element 102 in the form of an electric resistance element. Heat energy generated by the heating element 102 heats the gas passing through non-contact energy source 100. The heated gas is then directed out of the non-contact energy source 100 through energy directors 104 and 106 which may be e.g., tubes, or other fluid delivery apparatus. The fluid may be heated to a temperature of about 150° F. to about 800° F. It may be preferred that the fluid temperature be about 450° F. to about 550° F.

Although a common non-contact energy source 100 is depicted in FIG. 9 with its output used to treat the upper and lower beaks, it will be understood that, alternatively, two different non-contact energy sources may be used, with the heated fluid from one source being applied to the upper beak and the heated fluid from the second source being applied to the lower beak.

Although the beak treatment apparatus and methods are described herein are described as being implemented in a rotating system, it should be understood that the apparatus may alternatively be implemented in a stationary system in which each bird is located in a stationary fixture designed for beak treatment. Alternatively, the beak treatment apparatus and method may be implemented in a linear conveyor system.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments set forth herein and that such embodiments are presented by way of example only, with the scope of the invention intended to be limited only by the claims.

The invention claimed is:

1. An apparatus for treating the upper and lower beaks of a bird, the apparatus comprising:

a bird head positioning device comprising first and second major sides and a beak receiving aperture formed through the first and second major sides, the bird head positioning device adapted to position the head of a bird proximate the first major side, wherein the upper and lower beaks of the bird head protrude through the beak receiving aperture and are exposed proximate the second major side of the bird head positioning device;

a non-contact energy source emitting energy;

a primary energy director directing energy from the non-contact energy source at the second major surface of the beak locator, wherein energy emitted from the non-contact energy source is directly incident on the upper back exposed proximate the second major side of the bird head positioning device; and a secondary energy director redirecting energy from the primary energy director towards the lower beak exposed proximate the second major side of the bird head positioning device, wherein the secondary energy director comprises a focusing energy director, and wherein the energy redirected by the secondary energy director is incident on the lower beak exposed proximate the second major side of the bird head positioning device.

2. An apparatus according to claim 1, wherein the non-contact energy source comprises an electromagnetic energy source, and wherein the secondary energy director comprises a reflector adapted to reflect electromagnetic energy emitted by the electromagnetic energy source.

3. An apparatus according to claim 1, wherein the non-contact energy source comprises a bulb, and wherein the secondary energy director comprises a reflector adapted to reflect the electromagnetic energy emitted by the bulb.

4. An apparatus for treating the upper and lower beaks of a bird, the apparatus comprising;

a bird head positioning device comprising first and second major sides and a beak receiving aperture formed through the first and second major sides, the bird head positioning device adapted to position the head of a bird proximate the first major side, wherein the upper and lower beaks of the bird head protrude through the beak receiving aperture and are exposed proximate the second major side of the bird head positioning device;

a non-contact energy source emitting energy, wherein the non-contact energy source comprises a heated fluid source;

an upper beak energy director directing energy from the non-contact energy source at the second major surface of the beak locator, wherein energy directed by the upper beak energy director is directly incident on the upper beak exposed proximate the second major side of the bird head positioning device; and a lower beak energy director directing energy from the non-contact energy source at the second major surface of the beak locator, wherein energy directed by the lower beak energy director is directly incident on the lower beak exposed proximate the second major side of the bird head positioning device.

5. An apparatus according to claim 4, wherein the non-contact energy source comprises an electromagnetic energy source.

6. A method of treating the upper and lower beaks of a bird, the method comprising:

positioning a bird head in a bird head positioning device, wherein the bird head positioning device comprises first and second major sides and a beak receiving aperture formed through the first and second major sides, and wherein the upper and lower beaks of the bird head protrude through the beak receiving aperture and are exposed proximate the second major side of the bird head positioning device;

emitting energy from a non-contact energy source;

directing the energy emitted from the non-contact energy source at the second major surface of the bird head positioning device using a primary energy director, wherein the energy directed by the primary energy director is directly incident on the upper beak exposed proximate the second major side of the bird head positioning device; and redirecting energy from the primary energy director using a secondary energy director, wherein the energy redirected by the secondary energy director is incident on the lower beak exposed proximate the second major side of the bird head positioning device, and wherein redirecting energy using the secondary energy director comprises focusing the redirected energy on the lower beak.

7. A method according to claim 6, wherein the secondary energy director delivers less energy to the lower beak than the primary energy director delivers to the upper beak.

8. A method according to claim 6, wherein the energy emitted by non-contact energy source comprises electromagnetic energy, and wherein redirecting energy using the secondary energy director comprises reflecting the electromagnetic energy.

9. A method according to claim 6, wherein the energy emitted by non-contact energy source comprises laser energy.

10. A method according to claim 6, wherein the non-contact energy source comprises a bulb emitting electromagnetic energy, and wherein redirecting energy using the secondary energy director comprises reflecting the electromagnetic energy emitted by the bulb.

11. A method of treating the upper and lower beaks of a bird, the method comprising:

positioning a bird head in a bird head positioning device, wherein the bird head positioning device comprises first and second major sides and a beak receiving aperture formed through the first and second major sides, and wherein the upper and lower beaks of the bird head protrude through the beak receiving aperture and are exposed proximate the second major side of the bird head positioning device;

directing energy at the second major surface of the bird head positioning device using an upper beak energy director, wherein the energy directed by the upper beak energy director is directly incident on the upper beak exposed proximate the second major side of the bird head positioning device, and wherein the energy is absorbed by the upper beak in the absence of physical contact; and directing energy at the second major surface of the bird head positioning device using a lower beak energy director, wherein the energy directed by the lower beak energy director is directly incident on the lower beak exposed proximate the second major side of the bird head positioning device, and wherein the energy is absorbed by the lower beak in the absence of physical contact;

wherein the energy directed by the upper beak energy director and the energy directed by the lower beak energy director is emitted from a common non-contact energy source.

12. A method according to claim 11, wherein the lower beak energy director delivers less energy to the lower beak than the upper beak energy director delivers to the upper beak.

13. A method according to claim 11, wherein the energy directed by the upper beak energy director is emitted from an upper beak energy source, and wherein the energy directed by the lower beak energy director is emitted from a lower beak energy source.

14. A method according to claim 11, wherein the energy directed by the energy directed by the upper beak energy director and the energy directed by the lower beak energy director comprises electromagnetic energy.

15. A method according to claim 11, wherein the energy directed by the upper beak energy director and the energy directed by the lower beak energy director comprises a heated fluid.

16. A method according to claim 11, wherein the energy directed by the energy directed by the upper beak energy director and the energy directed by the lower beak energy director comprises laser energy.

* * * * *

UNITED STATES PATENT AND TRADEMARK OFFICE

CERTIFICATE OF CORRECTION

PATENT NO. : 7,232,450 B2
APPLICATION NO. : 10/346981
DATED : June 19, 2007
INVENTOR(S) : Marc S. Gorans et al.

It is certified that error appears in the above-identified patent and that said Letters Patent is hereby corrected as shown below:

In column 1, line 63, delete “tat” and replace with --that--.

In column 2, line 3, delete “tat” and replace with --that--.

In column 8, line 50, delete “are” and replace with --as--.

In claim 1, column 9, line 17, delete “back” and replace with --beak--.

In claim 14, column 12, line 2, delete “by the enegy directed”.

In claim 16, column 12, line 10, delete “by the enegy directed”.

Signed and Sealed this

Tenth Day of June, 2008

JON W. DUDAS
*Director of the United States Patent and Trademark Office*